United States Patent
Federici et al.

(10) Patent No.: US 7,354,765 B2
(45) Date of Patent: Apr. 8, 2008

(54) SOYA CELL STRAINS WITH HIGH ISOFLAVONE CONTENT

(75) Inventors: Ermanno Federici, Perugia (IT); Andre Touche, Monts (FR); Didier Courtois, St-Avertin (FR); Vincent Petiard, Tours (FR)

(73) Assignee: Nestec S.A., Vevey (CH)

( * ) Notice: Subject to any disclaimer, the term of this patent is extended or adjusted under 35 U.S.C. 154(b) by 436 days.

(21) Appl. No.: 10/962,074

(22) Filed: Oct. 7, 2004

(65) Prior Publication Data
US 2005/0050589 A1    Mar. 3, 2005

Related U.S. Application Data

(63) Continuation of application No. PCT/EP03/03863, filed on Apr. 14, 2003.

(30) Foreign Application Priority Data
Apr. 30, 2002 (EP) .................... 02009810

(51) Int. Cl.
  A01H 1/00      (2006.01)
  A01H 5/00      (2006.01)
  C12N 15/82     (2006.01)
  C12N 5/04      (2006.01)

(52) U.S. Cl. .............. 435/419; 435/420; 800/312
(58) Field of Classification Search ................ None
  See application file for complete search history.

(56) References Cited

U.S. PATENT DOCUMENTS 4,992,375 A * 2/1991 Wright ................ 435/426

OTHER PUBLICATIONS

Stopper, et al. (2005) Genotoxicity of Phytoestrogens. Mutation Research 574:139-155.*
Bouque (1998) Plant Cell, Tissue and Organ Culture 53:35-40.*
Jain (2001) Tissue culture-derived variation in crop improvement. Euphytica 118:153-166.*

(Continued)

*Primary Examiner*—Anne Marie Grunberg
*Assistant Examiner*—Brendan O. Baggot
(74) *Attorney, Agent, or Firm*—Bell, Boyd & Lloyd LLP

(57) ABSTRACT

The present invention relates to soya cell cultures and soya cell strains producing a high amount of isoflavones and to a process for preparing an isolating isoflavone compounds in high yields. The present invention also pertains to soya plants regenerated from such cell strains and the use thereof for obtaining isoflavone compounds.

6 Claims, 3 Drawing Sheets

OTHER PUBLICATIONS

Larkin, et al (1981) Somaclonal variation—a novel source of variability from cell cultures for plant improvement 60(4) 197-214.*

Lachman et al., (1990) Polyphenois And Isoflavonoids Of Soybean Glycine-Max L. Merr. Rostinna Vyroba, vol. 36, pp. 295-302.*

Bourgeais-Chaillou, et al. (1992) Comparative Effects Of Nitrogen-Sources On Growth And Physiological Responses Of Soyabean Exposed To Sodium Chloride-Stress. Journal of Experimental Botany, vol. 43, No. 254, pp. 1225-1233.*

K. Reinli et al., XP000878760, "Phytoestrogen Content Of Foods—A Compendium Of Literature Values". Nutrition And Cancer, vol. 26, No. 2, 1996, pp. 123-148,(1996).

XP002203167, USDA—"Iowa State University Database On The Isoflavone Content Of Foods—1999",pp. 1-19 (2002).

J. Liggins et al., XP001083859, "Daidzein And Genistein Contents Of Vegetables" British Journal Of Nutrition, vol. 84, No. 5, pp. 717-725, (2000).

* cited by examiner

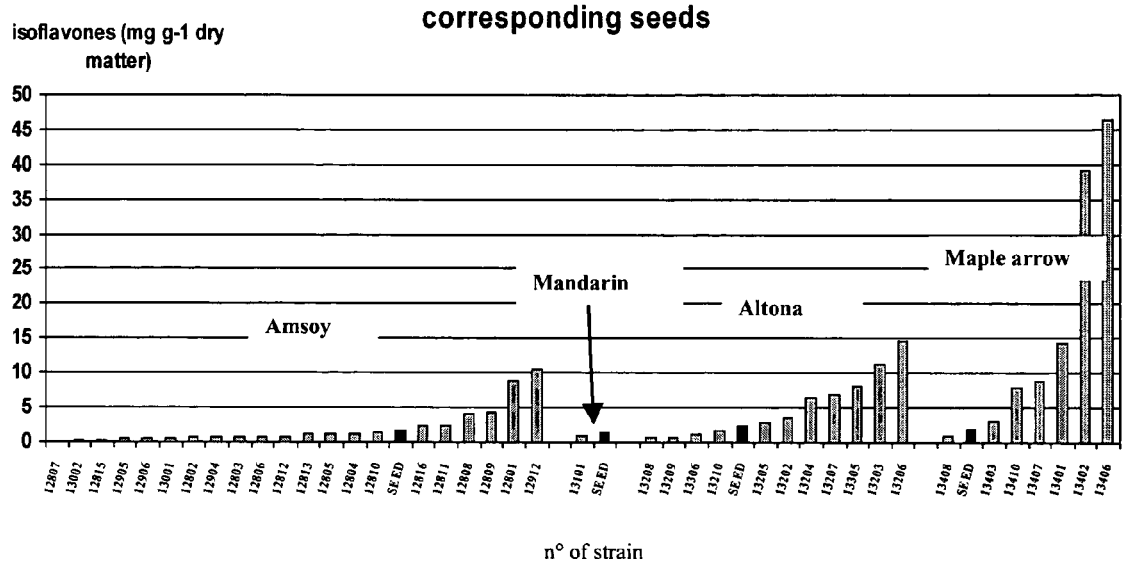
Fig 1: Total content in isoflavones in callus cultures and corresponding seeds
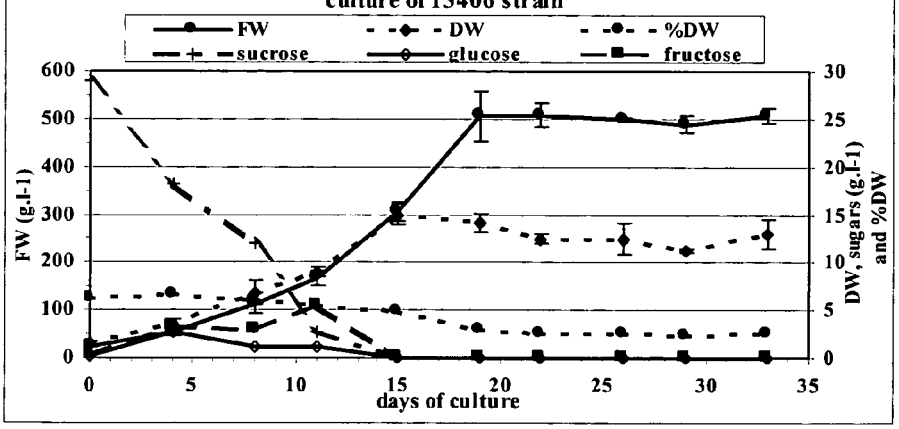
Fig.2: Kinetics of growth and sugar concentration in suspension culture of 13406 strain

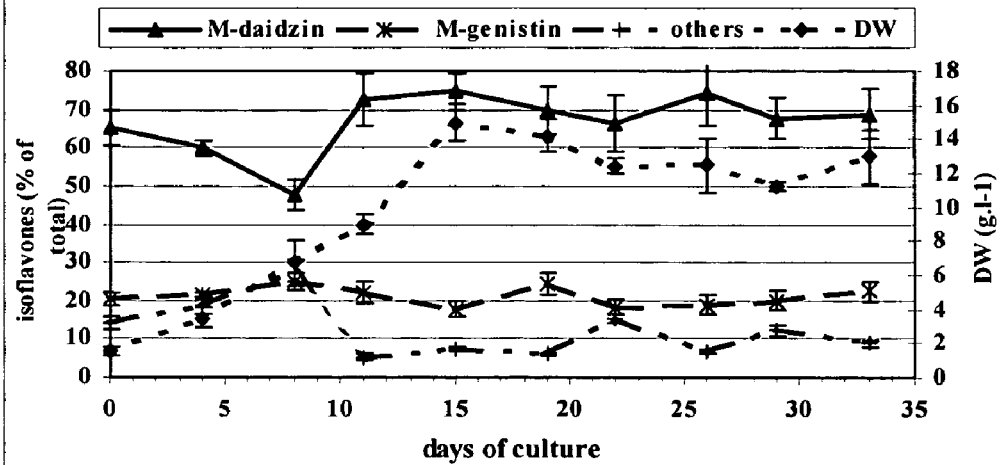
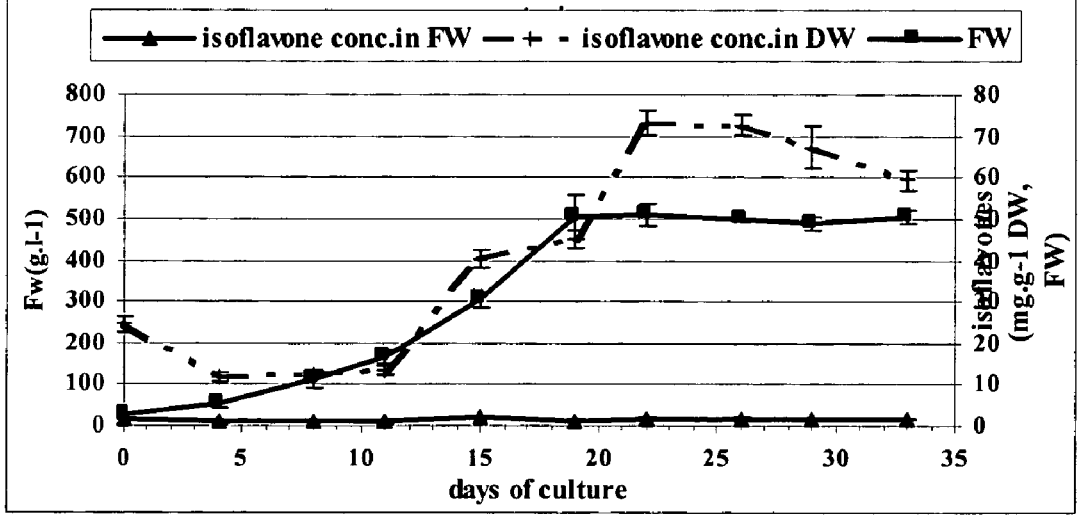

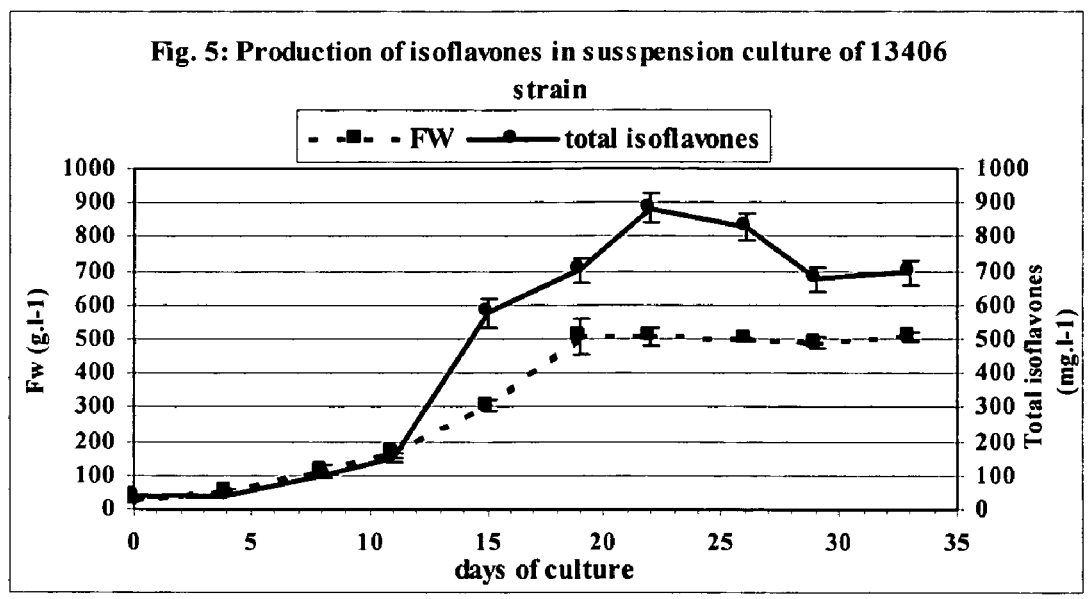

SOYA CELL STRAINS WITH HIGH ISOFLAVONE CONTENT

CROSS-REFERENCE TO RELATED APPLICATIONS

This application is a continuation of International application PCT/EP03/03863 filed Apr. 14, 2004, the entire content of which is expressly incorporated herein by reference.

BACKGROUND ART

The present invention relates to soya (Glycine max) cells and soya cell strains producing isoflavones at a high level and to a process for preparing and isolating isoflavone compounds in high yields. The present invention also pertains to soya plants regenerated from such cell strains and the use thereof for obtaining isoflavone compounds.

Isoflavones are a unique class of plant flavonoids that have a limited distribution in the plant kingdom and are chemically characterized as colorless, crystalline ketones. The most common source for this sort of compounds in nature are soybeans that essentially contain twelve isoflavone isomers: genistein, genistin, 6"-0-malonylgenistin, 6"-0-acetylgenistin, daidzin, daidzein, 6"-0-malonyldaidzein, 6"-0-acetylgenistin; glycitein, glycitin, 6"-0-malonylglycitin, 6"-0-acetylglycitin. The principal types of isoflavones found in soybeans are glycones (with sugars) and aglycones (without sugars). Glycones have a glucose molecule attached, and include genistin, daidzin and glycitin, while aglycones are isoflavones without the glucose molecule and include genistein, daidzein and glycitein.

In the recent past isoflavones have been found to exert a number of beneficial effects on living beings upon ingestion. They are deemed to be at least partly responsible for the commonly accepted characteristic of soybeans to reduce the cholesterol level in mammals (Setchell, in McLachlan J A, ed. Estrogens in the Environment II (1985), 69-85). Studies with primates suggest that soya isoflavones may even account for up to about 60-70% of said hypocholesterolemic property (Anthony et al., Circulation 91 (1995), 925). Since coronary heart disease (CHD) is a leading cause of death, especially in the industrialized nations, elevated total cholesterol and low density lipoprotein (LDL) levels are important risk factors for CHD. In humans, soy protein products appear to lower serum total cholesterol levels and low-density lipoprotein (LDL) cholesterol by an average of about 10% when consumed at an average intake level of 47 g soy protein per day.

It has also been suggested that isoflavones participate in the prevention of certain types of cancers. It had statistically been recognized that Japanese women, who due to food intake almost daily consume soy protein, appear to have a quite lower incidence of breast cancer as compared to occidental individuals (Adlercreutz et al., J. Nutr. 125 (1995), 757S-770S). As a scientific confirmation, in animal models, a decrease of mammary tumor formation or inhibition of mammary tumor progression could be revealed when feeding soy protein to rats (Barnes et al., Clin. Biol. Res. 347 (1991), 239-253).

In particular, genistein has been proven to inhibit protein tyrosine kinase (Akiyama et al., J. Biol. Chem. 262 (1987), 5592-5595), to inhibit angiogenesis (Fotsis et al., Proc. Natl. Acad. Sci. USA 90 (1993), 2690-2694), and to induce differentiation in several malignant cell strains (Peterson, J. Nutr. 125 (1995), 784S-789S), all of which are deemed to be important risk factors in cancer development. Genistein and biochanin A are presumed to also inhibit the growth of androgen-dependent and independent prostatic cancer cells (Peterson and Barnes, Prostate 22 (1993), 335-345,) and to act as an antioxidant (Wei et al., Nutr. Cancer 20 (1993), 1-12).

Beyond cancer, it is also thought that at least some of the soya isoflavone fractions are especially beneficial for women in general since they are sources of plant estrogen. It is believed that plant estrogen provides many of the advantages and avoids some of the alleged disadvantages of animal estrogen, so that isoflavones have been proposed to be used for treating menopausal disorders.

So far research has revealed that the pharmacological effects of isoflavone compounds are primarily attributed to their aglycones, such as daidzein or genistein. Specifically, of the soybean isoflavone aglycones genistein has recently been shown to be particularly excellent in physiological activities, including antiosteoporosis activity, antiarteriosclerotic activity, and anticancer activities in the breast, the stomach and the prostate (S. Barnes, Biochem. Biophys. Res. Commun. 179 (1997), 661).

Hence, in view of the known beneficial effects the provision of isoflavones in high amounts is a constant and increasing desideratum.

In the art several methods have been proposed to isolate isoflavones with the first successful attempt dating back to 1931 (Justus Liebigs Ann. Chem 489 (1931), 118).

In U.S. Pat. No. 5,702,752 a process for recovering isoflavone values from a soya molasses feed stream is disclosed. The process comprises subjecting an aqueous soya extract to ultrafiltration to recover the isoflavones as a permeate and further purifying the isoflavones by conventional means.

U.S. Pat. No. 5,821,361 discloses an alternative method for recovering isoflavones from soya molasses. A solution of soya molasses in water is treated at a pH and temperature to convert isoflavone conjugata to isoflavone glucosides, precipitating the isoflavone glucosides and separating the isoflavone glucosides from the solution by filtration and centrifugation.

In addition, JP-05176756A discloses the recovery of isoflavone derivatives from soya based materials by extracting the soya based material with 80% methanol.

A substantial drawback of all the prior art methods resides in that the starting material, the soybean, merely provides a limited amount of isoflavone per unit material utilized to approximately 0.1 to 0.5% dry weight which eventually restricts the amount available and increases the extraction cost. In addition, the level of isoflavones in soybean varies between the years by 3 to 8 fold, which fact is aggravated in that between varieties the level may also vary by about 2 to 3 fold.

A problem of the present invention therefore resides in overcoming the shortcomings of the prior art and providing an improved method for constantly obtaining high amounts of isoflavone compounds. Thus, there is a need for resolving these prior art problems and these are provided by the present invention.

SUMMARY OF THE INVENTION

The above problem has been solved by providing a soybean cell culture or cell strain, respectively that inherently produces high amounts of isoflavones.

The present invention also provides a process for preparing or isolating isoflavones from soya, which comprises using as a starting material a cell strain according to the present invention, or a plant derived therefrom.

The invention also relates to a soya plant cell culture or cell strain expressing a content of isoflavones exceeding 25 mg/g dry matter and preferably exceeding 35 mg/g dry matter. Also, the cell contains more than 70% of isoflavones as glucoside-malonylated conjugates, wherein the malonyl-daidzin content is between 60 and 80% of the total isoflavones and the malonylgenistin content is between 5 and 30% of the total isoflavones.

The invention also relates to a soya plant cell strain which is DSM 14883.

The new soya plants can also be regenerated from a soya plant cell or cell strain according to the invention disclosed herein.

The invention also relates to a method of producing a food product or food supplement enriched in isoflavones, malonyldaidzein and/or malonylgenistein which comprises growing a plant from a raw material comprising the soya plant cell or regenerated plant according to the invention disclosed herein.

The method of producing isoflavones comprises growing a plant from a raw material comprising the soya plant cell or regenerated plant according to the invention herein, and the isoflavones are then recovered from the plant. In this method, the plant cell culture or cell strain is typically cultivated in a bioreactor. The isoflavones are obtained by extraction with a solvent, preferably one based on a EtOH/water or MeOH/water mixture.

BRIEF DESCRIPTION OF THE DRAWING FIGURES

The appended drawing figures illustrate preferred features and performance of the invention. In these figures:

FIG. 1 shows the results of an experiment investigating the total content of isoflavone in different soya cell strains;

FIG. 2 shows the kinetics of growth of a cell strain of the present invention;

FIG. 3 shows the distribution of isoflavones in a cell strain according to the present invention;

FIG. 4 shows the results of experiments investigating the production of isoflavones in a cell strain according to the present invention;

FIG. 5 shows the results of experiments investigating the production of isoflavones in a cell strain according to the present invention.

DETAILED DESCRIPTION OF THE PREFERRED EMBODIMENTS

As will be appreciated, the present invention is based on the surprising finding that soya cell strains are present that synthesize isoflavones in a high amount, by far exceeding that found in soybean, so that these cell strains may be used as a production tool of isoflavones. In the context of this application the terms "cells" and "cell strains" are used interchangeably. These cell strains do, therefore, provide a starting material for the isolation of isoflavones that enables to obtain high yields with only a low amount of starting material, while concurrently providing a constant amount of said substances without being subject to yearly changes in their synthesis in the plant.

In the context of the present invention the term "high amount" is meant to indicate an amount of at least about 25 mg/g dry matter of cells, preferably at least 35 mg/g dry matter of cells, more preferably at least 45 mg/g dry matter of cells.

Preferably, the cell strains of the present invention contain more than 90% of isoflavones as glucoside-malonylated conjugates. According to an alternative preferred embodiment malonyldaidzin is synthesized in an amount of between about 60 and 80% of the total isoflavones, with malonylgenistin being synthesized in an amount of about between 5 and 30% of the total isoflavones.

According to a most preferred embodiment the present invention pertains to a cell strain that has been deposited according to the Budapest Treaty with the DSMZ (Deutsche Sammlung von Mikroorganismen und Zellkulturen GmbH, Mascheroder Weg 1b, D-38124 Braunschweig, Germany) on 27.02.2002, which received the deposit number DSM 14883.

The cell strains of the present invention may be utilized for regenerating a soya plant which also will synthesize a higher isoflavone content as compared to known soya plants. Methods for preparing plants from single plant cells are well known in the art and include the steps of in vitro shoot regeneration, then rooting, or somatic embryogenesis then germination with appropriated culture media and acclimatization in greenhouse.

The cell strain collection is preserved as callus cultures on solid medium. Nevertheless, preferably, the cell strains of the present invention are cultured in liquid medium (identical to the ones used for callus cultures but without gelling agent, such as agar) in a bioreactor under conditions suitable for the growth of the cells and the synthesis of the desired compounds. Suitable conditions are e.g. utilizing the basal Gamborg et al. medium (Gamborg O. L., Miller R. A. and Ojima K., 1968. Nutrient requirements of suspension cultures of soybean root cells. Exp. Cell Res. 50, 151-158) or the Murashige and Skoog medium (Murashige R. and Skoog F., 1962.: A revised medium for rapid growth and bioassays with tobacco tissue cultures. Physiol. Plant., 15, 473-497), added with plant hormones e.g. utilizing auxines (2,4-dichlorophenoxyacetic acid 2,4-D or naphtaleneacetic acid NAA or indole acetic acid IAA) and cytokinines (benzyladenine or benzylaminopurine) and sugars (e.g. sucrose, glucose at 20 to 60 g/liter). pH is 5 to 6 units, and temperature between 20° and 30° C.

The cells can be cultivate as "callus cultures" in petri dishes on solid medium (medium added with agar or Gelrite) and subcultured every month. These calli can be easily transferred in agitated liquid medium (Erlenmeyer flask) to obtain a cell suspension culture which is subcultured every 15 to 21 days. These cell suspensions are used for mass cell cultures in bioreactors.

Due to the stability of the cells or cell strains of the present invention a continuous and uniform production of isoflavones is provided with a high quality and yielding amounts per unit material higher as compared to the systems of the prior art. In soya plants commonly utilized for the isolation of isoflavones the levels of isoflavones normally varies between the years by 3-8 fold and 2-3 fold between varieties. Up to the present invention it was therefore difficult to obtain isoflavone extracts from soybean exhibiting a reproducibly constant amount thereof.

Moreover, extracts isolated from soya plants also contain relative high levels of bitter components, saponins and typically these isoflavone compounds have been associated with an inherent, bitter flavor. Due to the inherent high concentration of isoflavones in the cells of the present invention impurities relating to such bitter components are reduced to a minimum. Also, the cost of pure isoflavone compounds, which normally may reach very high levels, may be reduced, since less starting material has to be subjected to an isolation procedure (to yield the same amount of isoflavones) and the number of purification steps (in particular to get rid of bitter components) may be reduced, since the ratio isoflavones-impurities has already been shifted versus the desired compounds in the starting material. As an example, genistein, an inhibitor or protein tyrosine kinase (PTK), chemically synthesized or genistein extracted from soybeans currently may cost up to $ 5,000,00 per gram. According to the present invention these drawbacks of the prior art may all be overcome, due to the level and stability of the expression of the subjective compounds.

Once the cells/calli have been cultured to a desired density they are harvested and subjected to a procedure for extracting and purifying the isoflavones, which may comprise using a mixture of ETOH and water or methanol as an extraction solvent, followed by a purification on synthetic adsorbants (for examples analytical cartridges Waters Seppack C18 or polymeric resins as XAD2, polyamine MN SC6 and elution by selective solvent such as EtOH or MeOH).

Consequently, the cells or cell strains and even the beans from plants derived therefrom may be utilized for isolating isoflavones, which will eventually give higher yields even when starting with a minor volume of starting material while concurrently saving costs.

Once obtained, the isoflavone compounds may be incorporated into the desired products, such as nutritional products or pharmaceuticals in a manner known per se.

EXAMPLES

The following examples illustrate the invention without limiting it thereto.

Tissue Cultures:

As control, seeds of the different cultivars were analyzed in parallel with the tissue culture.

Tissue culture strains of Glycine max (L.) Merr. were initiated 25 years ago from cotyledons of different cultivars on Gamborg et al. medium (1968) supplemented with 20 g/l sucrose, 7 g/l agar (bacto-agar Difco) and 1 mg/l 2,4-D. The pH was adjusted to 5.8 prior to autoclaving (20 min at 115° C.). 40 strains were subcultured on the same medium in Petri dishes (10 cm diameter) monthly and placed at 26° C. under light (16 h photoperiod, 36 µmol/m$^2$s, cool white fluorescent lamps, Sylvania Groslux, Germany). 21 were initiated from cv. Amsoy, 11 from Altona, 7 from Maple arrow and 1 from mandarin, respectively.

One strain (13406, cv. Maple arrow) was transferred in liquid medium (same medium as for tissue cultures without agar and 30 g/l sucrose) and subcultured in 250 ml Erlenmeyer flask (5 g fresh weight with 100 ml medium) every two weeks, under the same conditions as with the tissue culture collection. The Erlenmeyer flasks were placed on an orbital shaker (New Brunswick Scientific, Edison, USA) at 100 rpm (shaking diameter 20 min).

As a bioreactor, 10l stirred bioreactor (New Brunswick Scientific) with two six bladed stirrer turbines, was used under the same conditions of medium, temperature and pH as above. Antifoam (Silbione 70414, Rhône-Poulenc Chimie, France) at 50 mg/l was added before sterilization. The bioreactor containing 9.6l of fresh medium was autoclaved 40min at 115° C. Seven days old cells were filtered from two 1l Erlenmeyer flasks (400 ml medium).

300 g fresh matter was put into a 1l Erlenmeyer flask (400 ml fresh medium) with a specific output to be connected to the bioreactor. The stirring rate was 100 rpm. Dissolved oxygen was maintained at 30% using a biocontroller (SGI company, France) equipped with a sterilizable oxygen probe (Ingold), and a mass flowmeter (SGI). Fresh medium was supplied continuously if needed with a peristaltic pump (SGI). In this case, the effluent was automatically removed via a solenoid valve which was controlled by a medium level probe, allowing the air overflow and the harvest. When the level of the medium was higher than the limit fixed by the probe level, a timer opens the valve for 30 min. Then the harvest occurred and stopped as soon as the probe was disconnected to the medium. By this way, semi-continuous or continuous cultures could be performed.

Sampling, Extraction and Analysis

Growth measurements: Dry weight was obtained after freeze-drying of an aliquot biomass sampled for the determination of the fresh weight. Sugars (sucrose, glucose, fructose) were determined enzymatically with the Assay Reagent Kit from Roche Molecular Biochemicals, USA (n°716260).

Extraction and analysis: 1 g of freeze-dried cell culture was ground in a mortar, mixed with 1 g of celite and packed into a 25 ml plastic column, between two frits. 50 ml of MeOH-water (80/20, v/v) were sucked through the sample in the column and the extract obtained was filtered through a 0.45 µm membrane filter prior to injection in the HPLC system. For callus cultures, the first evaluation of the isoflavone content was performed at the time of subculture (1 month). The experiments were performed in triplicate. For the evaluation all over the culture time, 3 Petri dishes were harvested per experimental points and analyzed separately. For cell suspension cultures, the same procedure was followed, using 3×250 ml Erlenmeyer flask per experimental point.

Analysis of isoflavones: HPLC separation of isoflavones was performed using a Nucleosil 100-C18 column (250 mm×4.3 mm, Macherey-Nagel 720014). An elution was carried out at a flow rate of 1.0 ml/min at room temperature, with a linear gradient composed of (A) pure acetonitrile and (B) 0.05% phosphoric acid in water. Following injection of 20 µl of sample, solvent A was increased linearly from 10 to 50% for 40 min, then 50 to 100% for 3 min and held at 100% for 5 min. The column was reequilibrated running for 10 min at the initial conditions before proceeding with the following injection. Analyses were monitored with a photodiode array detector at 258 nm, scanning between 220 and 400 nm for peak identification. Controls were daidzin, genistin, daidzein and genistein from Extrasynthése, France, and malonyldaidzin and malonylgenistin were purified from soybean extracts. Retention times were 12, 15.7, 16.3, 19.7, 21.4 and 26.8 min for daidzin, genistin, malonyl-daidzin, malonyl-genistin, daidzein and genistein, respectively.

Callus Cultures

FIG. 1 represents the isoflavone content observed in the collection of 40 different strains at the time of subculture, according to the cultivar of origin. A great variability of isoflavone content is observed within these strains, from 0.10 mg/g DW (n°12807) to 46 mg/g (n°13406). It is not possible to conclude for an effect of the cultivar of origin due to a too small population for each. In seeds from the same varieties, the isoflavone content is never higher than 2.5 mg/g. In cell culture and seeds, glucoside-malonylated conjugates were always the major compounds.

Suspension Cultures

The surprising high isoflavone content observed in the Maple arrow strain 13406 led us to select this strain for experiments in liquid medium in Erlenmeyer flask and 10l bioreactor in order to characterize the accumulation of isoflavones. Calli were transferred in liquid medium and cultivated under the same culture conditions than those on solid medium except they were agitated.

Cell suspension was growing with a $\mu max=0.158$ $d^{-1}$ up to 500 g/l (fresh weight) and 14.5 g/l (dry weight) (FIG. 2). The lag phase is relatively long (3-4 days, due to the low inoculum density (25 g/l), and reduced to 1-2 days if the inoculum density is 50 g/l. Kinetics are similar for FW and DW. Nevertheless, the dry matter content decreased regularly, showing that cells became more turgescent along the culture time. This may have an effect on the capacity of accumulation of isoflavones. Initial sucrose is hydrolyzed regularly in glucose and fructose, glucose being consumed preferentially. The absence of sugars is well corresponding with the beginning of the steady state of growth at day 15, signifying that sugars are at least one of the first limiting factors for growth.

Distribution of isoflavones (FIG. 3): Except with slight differences during the first days of cultures which correspond to the lag phase and beginning of the growth phase, the ratios remains stable, with 70% of malonyl-daidzin, 20% of malonyl-genistin and 10% of other forms (mainly daidzin and genistin and traces of daidzein and genistein). These results are very similar to those obtained with callus culture of the 13406 strain (Table 1).

These contents were surprisingly up to 1000 fold higher than those published in the prior art (e.g. Ames et al., Continuous production of daidzein and genistein from soybean in a magnetofluidized bed bioreactor, Biotechnology Progress, 13, 3 (1997), 336-339, who obtained 10 to 200 µg/g DW).

Isoflavone production (FIG. 5): The increase of the isoflavone content per biomass unit, combined with the increase of total biomass allowed to reach up to 880 mg/l of total isoflavones. This accumulation is regular along the growth phase, and there is no apparent degradation during the stationary phase.

The high-producing strain (13406) has been studied for 2 years by now in liquid medium, without any decrease of its potential to accumulate isoflavones.

Accordingly a specific balance in glucoside-malonylated conjugates may be obtained. In the aim of a specific production of isoflavones by plant cell cultures of soya, the present work shows that it is possible to reach high content (7% DW), high concentration (880 mg/l) and productivity (60 mg/l d) in erlenmeyer flask and bioreactor.

What is claimed is:

1. A soya plant cell strain expressing a content of isoflavones exceeding 25 mg/g dry matter, wherein the soya plant cell strain has depositary accession number DSM 14883.

2. The soya plant cell strain according to claim 1, wherein the content of isoflavones exceeds 35 mg/g dry matter.

3. The soya plant cell strain according to claim 1, wherein more than 70% of isoflavones in the cells are glucoside-malonylated conjugates.

TABLE 1

Distribution of isoflavones in calli and seeds (% of total)

| | callus 13406 | callus 13403 | callus 13407 | seeds Vinton | seeds Mandarin | seeds Altona | Seeds Amsoy | seeds Maple |
|---|---|---|---|---|---|---|---|---|
| Aglycones | | | | | | | | |
| Daidzein | 3.28 | 1.64 | 0.23 | t | t | t | t | t |
| genistein | 0.79 | 0.68 | 0.48 | 4.79 | 9.17 | t | 5.72 | 0.81 |
| Glycitein | 0.06 | 0.93 | t | t | t | t | t | t |
| Glucosides | | | | | | | | |
| Daidzin | 6.26 | 3.58 | 3.89 | 7.65 | 8.30 | 7.14 | 8.64 | 8.01 |
| Genistin | 1.90 | 1.52 | 6.87 | 8.64 | 8.09 | 9.92 | 8.38 | 7.04 |
| Glycitin | 0.22 | t | t | t | t | t | t | t |
| malonyldaidzin | 60.88 | 61.22 | 26.74 | 35.77 | 30.83 | 33.98 | 36.04 | 34.06 |
| malonylgenistin | 26.61 | 30.43 | 61.80 | 43.15 | 43.61 | 48.96 | 53.13 | 50.08 |
| malonylglycitin | t | t | t | t | t | t | t | t | t = traces

Isoflavone concentration (FIG. 4): Up to 72 mg $g^{-1}$ DW has been obtained, higher than in callus culture. The concentration in isoflavones related to the FW increased only two fold during the growth after 4 days of culture (0.8 to 1.6 mg/g FW), whereas it increased 6.5 fold related to the DW (11 to 72 mg/g DW). This last curve is parallel to the FW curve. The accumulation rate is 5.3 mg/g DW $d^{-1}$ constant from day 10 to day 25. Isoflavones were accumulated all along the growth phase, and the volume of the cells also conditions their final concentration.

4. The soya plant cell strain according to claim 1, having a malonyldaidzin content of between 60 and 80% of the total isoflavones.

5. The soya plant cell strain according to claim 1, having a malonylgenistin content of between 5 and 30% of the total isoflavones.

6. A soya plant regenerated from the soya plant cell strain according to claim 1.

* * * * *